United States Patent
Huston

(10) Patent No.: US 6,207,873 B1
(45) Date of Patent: *Mar. 27, 2001

(54) SKIN PROTECTOR

(76) Inventor: Trevor Lee Huston, 452 Longwood Dr., Venice, FL (US) 34292

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/156,587

(22) Filed: Sep. 18, 1998

(51) Int. Cl.[7] ............... A61F 13/00; A61F 5/44
(52) U.S. Cl. ............... 602/41; 602/45; 602/48; 602/57; 604/332
(58) Field of Search ............... 602/41, 42, 43, 602/45, 47, 48, 52; 604/366, 367, 368, 304, 307, 308, 180; 36/43, 44

(56) References Cited

U.S. PATENT DOCUMENTS

| | | | |
|---|---|---|---|
| Re. 29,453 | * 10/1977 | Weddle . | |
| 3,931,819 | * 1/1976 | Weddle | 604/344 |
| 4,373,519 | * 2/1983 | Errede et al. . | |
| 4,713,069 | * 12/1987 | Wang et al. . | |
| 4,758,239 | * 7/1988 | Yeo et al. . | |
| 5,154,960 | * 10/1992 | Mucci et al. | 428/68 |
| 5,156,601 | * 10/1992 | Lonenz et al. | 602/41 |
| 5,203,806 | * 4/1993 | Broida | 604/338 |
| 5,380,260 | * 1/1995 | Blott . | |
| 5,507,721 | * 4/1996 | Shippert | 602/46 |
| 5,538,500 | * 7/1996 | Peterson | 602/48 |
| 5,602,183 | * 2/1997 | Martin et al. . | |
| 5,652,274 | * 7/1997 | Martin | 514/720 |
| 5,674,521 | * 10/1997 | Gehrke et al. | 424/423 |
| 5,807,295 | * 9/1998 | Hutcheon | 602/42 |
| 5,998,695 | * 6/1998 | Roe et al. . | |

* cited by examiner

*Primary Examiner*—John G. Weiss
*Assistant Examiner*—Carie Mager
(74) *Attorney, Agent, or Firm*—Gifford, Krass, Groh, Sprinkle, Anderson & Citkowski, P.C.

(57) ABSTRACT

A guard for isolating patient skin from a medical appliance is formed from a nonwoven fiber web member soft nonadhesive material having a medication dispersed throughout the member. A continuous adhesive layer is attached to a planar surface of the nonwoven fiber web member suitable for attachment to a medical device so as to place the nonwoven fiber web member between the medical appliance and patient skin. The medication within the nonwoven fiber web member releases medicated powder to alleviate skin abrasion and chafing associated with prolonged contact with the medical appliance.

15 Claims, 2 Drawing Sheets

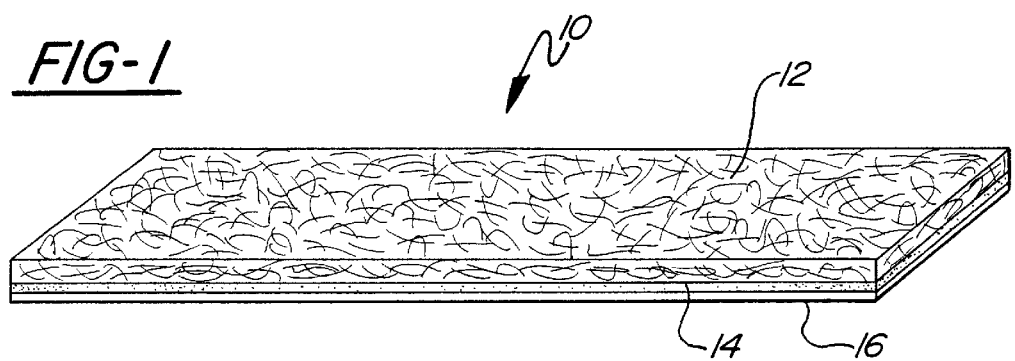
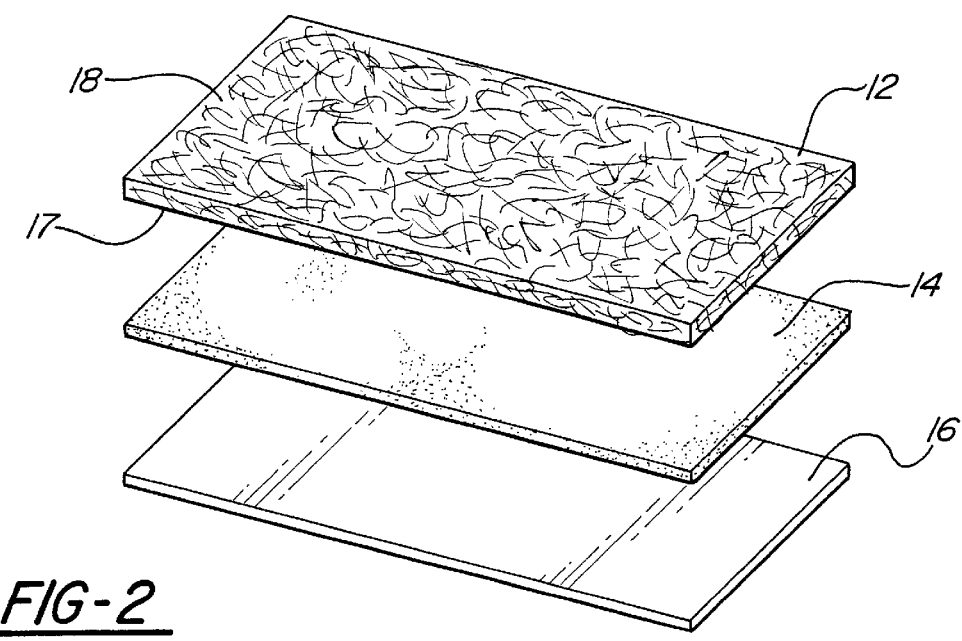
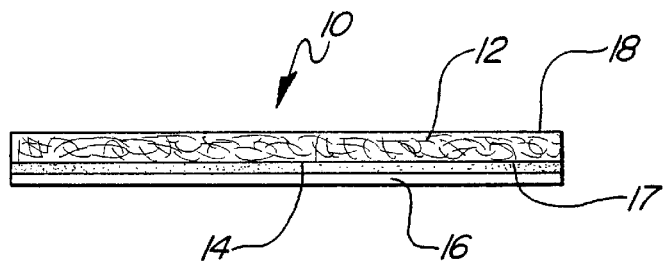

FIG-3
FIG-4
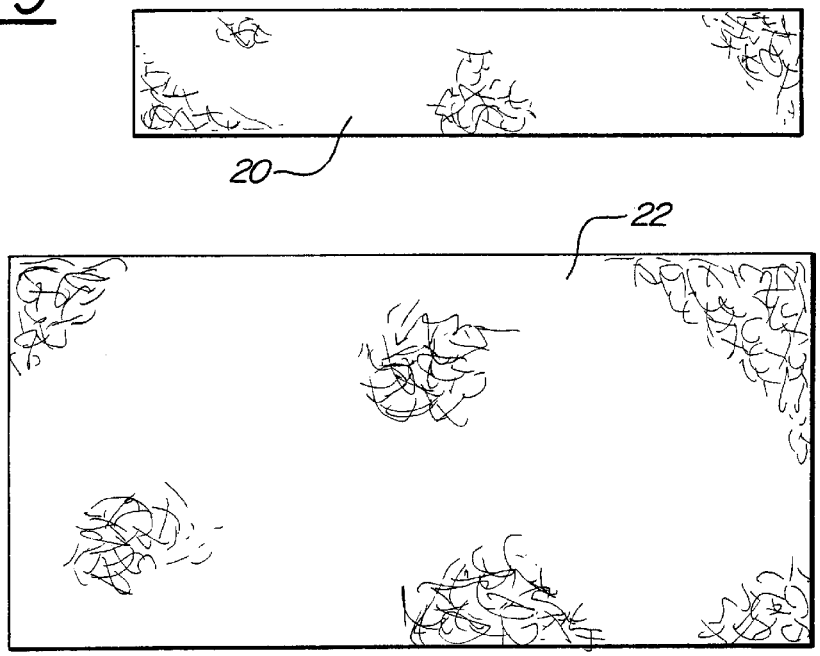
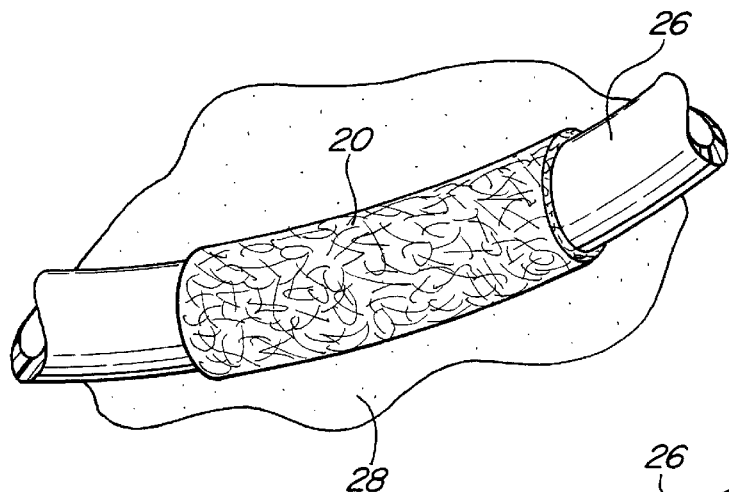
FIG-5
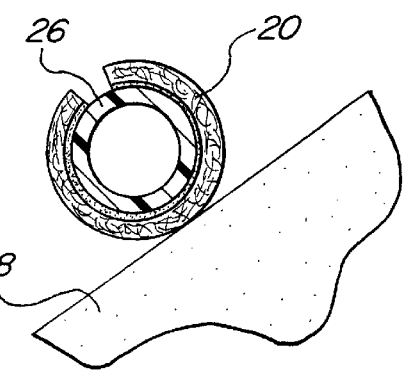
FIG-6

SKIN PROTECTOR

FIELD OF INVENTION

This invention relates to patient care devices and particularly to a skin protector which can be removably attached to medical treatment equipment such as tubes, bags, identification bands and the like.

BACKGROUND OF THE INVENTION

Plastic tubing is widely used for intravenous feeding of fluids and medication and in such procedures, the tubing comes into contact with the patient's skin. After a period of time such contact often causes pressure sores or chafing. Similarly, bags of plastic for colostomies and incontinence come into contact with a patient's skin and after a period of relative movement can cause chafing and discomfort and can lead to growth of bacteria. Another example of patient care accessories which can cause chafing are identification bands or bracelets. With these and other medical devices, it is desirable to avoid chafing by providing a guard or barrier between the device and the skin of the patient and a means for applying powder such as corn starch to avoid friction or other medication including zinc oxide or calcium undecylenate to reduce the effect of irritants.

It is an object of the invention to provide a means for isolating a medical device such as plastic tubing or bags from the skin of a patient to avoid chafing and pressure sores.

Another object of the invention is to provide a chafe guard which can be attached to selected locations on patient care devices which otherwise may come into direct contact with the skin of a patient.

Still another object of the invention is to provide a chafe guard or skin protector which prevents a medical or patient care device from coming into direct contact with the patients skin and which also can be used as an applicator for medicated powder to avoid friction and assist in treating or avoiding chafing of the skin.

SUMMARY OF THE INVENTION

The objects of the invention are attained by a skin protection chafe guard in the form of a planar body member of soft, cushion like material, such as nonwoven webbing of polyester fibers having a substantially uniform thickness. One side surface of such a body member is covered with a pressure sensitive adhesive which is temporarily covered with a removable and disposable sheet of releasable material. The body member may take various forms such as elongated strips which are adapted for attachment to tubing or large pads which may be cut to accommodate various shaped areas on bags or other patient care devices. After the appropriate shape of a body member is selected, the disposable sheet may be peeled away to expose the pressure sensitive adhesive surface for application to the surface of the tubing or other medical or patient care device that may contact the skin of the patient. This leaves the opposed surface of the body member exposed for soft, comfortable contact with the skin of a patient to resist and avoid chafing. The cushion-like body member can contain and release medicated powder to further alleviate skin abrasion and chafing. Also, the body member may be removed from the tubing or other medical device when it becomes soiled or worn. This is made possible by an adhesive which remains attached to the body member but separates cleanly from the tubing or other medical device to which it has been attached.

BRIEF DESCRIPTION OF THE DRAWINGS

FIG. 1 is a perspective view of the skin protecting device embodying the invention;

FIG. 2 is an exploded view of the skin protecting device seen in FIG. 1;

FIG. 2a is an end view, at an enlarged scale, of the device shown in FIG. 2;

FIG. 3 is a plan view of the skin protecting device embodying the invention;

FIG. 4 is a variation of the preferred embodiment of the invention shown in FIG. 3;

FIG. 5 is a perspective view of the skin protecting device seen in FIGS. 1–3 applied to a plastic tube; and FIG. 6 is a cross sectional view of the arrangements seen in FIG. 5 in relation to the skin of the patient.

DETAILED DESCRIPTION

Referring to the drawings, a preferred embodiment of the invention is designated generally in 10 and includes a body member 12 of soft, resilient material having a generally rectilinear shape and a substantially uniform thickness. One surface of the body member is covered with a layer of pressure sensitive adhesive 14 which remains permanently attached to the body member 12. The adhesive layer 14 is covered with a sheet 16 of releasable material to prevent contamination of the adhesive 14 and premature or accidental attachment to objects. The sheet 16 is removed to expose the adhesive 14 just prior to attachment to a device which is likely to come in contact with the skin of a patient. The layer of adhesive 14 and sheet of covering material 16 have been exaggerated in thickness in the drawings for purposes of clarity.

The body member 12 can be made of any appropriate gauze like material suitable for a medical environment. In a preferred embodiment of the invention, the body member 12 was made of a non-woven fibre web made up of polyester filaments having an approximate length of 3". The body member has an approximate uniform thickness of 3/16" in a non-compressed state with opposed planar surfaces 17 and 18 as seen in FIG. 2a. Such material is available from A. Foss Manufacturing Company, Inc., Hampton, N.H..

The assembly forming the skin protector 10 and including the body member 12, adhesive 14 and cover sheet 16 can be formed into strips 20 as seen in FIG. 3, which by way of example can have an approximate width of 7/8" and a length of 5" or into rectangular pads 22 as seen in FIG. 4 having for example a 3" width and a 6" length. The narrower strips 20 are satisfactory for application to plastic tubing 26 of smaller diameters as seen in FIG. 5. The pads 22 are appropriately used on the surface of plastic bags or straps. Moreover the larger pads can be cut or trimmed to better fit specific areas on the medical device to be isolated from the patients skin.

In use, an elongated protector 20 or a rectangular protector 22 is selected. After the protective covering sheet 16 is removed from the adhesive 14, that the body member 12 can be applied to the selected area of a medical device or tubing 26 that may come in contact with the skin of the patient by simply placing the body member 12 in the appropriate position and pressing it against the medical device, this is sufficient to maintain the protector in position, with the surface 18 facing the skin of the patient. In FIGS. 5 and 6 a skin protecting device 20 is shown as it might be applied to a plastic tubing 26 at a location likely to contact the skin of a patient as indicated at 28.

After a period of use, the body member 12 may become soiled or slightly compressed and it may be desirable to remove and replace the skin protector 10 from the medical device. This is accomplished by simply peeling the skin protecting device from the medical appliance. The adhesive readily separates without leaving any residue on the medical appliance so that it is in readiness for the application of another skin protecting device.

If desired, the body member 12 may be impregnated with medicated powder including corn starch and zinc oxide. The powder helps keep sensitive skin dry. Also, the powder helps relieve, treat and prevent rash and chafing.

Even without the powder medication, the body member 12, when applied to a medical appliance, is very useful in preventing chafing and abrasion of the skin. Such action is further enhanced with the use of powdered medication which is easily suspended in the body member for dispensing at surface 18 to the skin of the patient.

The pad form of protective device 22 shown in FIG. 4 can be applied to medical appliances such as plastic bags to cover large surfaces that may contact the skin and if desired can easily be trimmed with scissors to fit various shapes.

What is claimed is:

1. Medical tubing in combination with a guard for isolating patient skin from said tubing, the combination comprising:
   a. medical tubing; and
   b. a guard consisting of a non-woven fiber web member of soft non-adhesive material, having a first and a second opposing planar surfaces, wherein said non-woven fiber web member has a medication dispersed throughout; and a continuous adhesive layer of uniform thickness attached to the first planar surface of said non-woven fiber web member for attachment to an outer surface of said medical tubing so as to place said non-woven fiber web member at a location between said medical tubing and the patient skin so that the second surface having said medication thereon contacts the patient skin.

2. The combination of claim 1 wherein said continuous adhesive layer cleanly separates from said medical tubing.

3. The combination of claim 1 wherein said fibers are of polyester material.

4. The combination of claim 1 wherein said medication is in a powder form.

5. The guard of claim 4 wherein said powder is calcium undecylenate.

6. The combination of claim 4 wherein said powder is zinc oxide.

7. The combination of claim 1 wherein said non-woven fiber web member and adhesive layer are formed into elongated strips.

8. The combination of claim 1 wherein said non-woven fiber web member and adhesive layer are in the form of a rectilinear pad.

9. The combination of claim 3 wherein said filaments are of substantially uniform length.

10. Medical tubing in combination with a guard for isolating patient skin from said tubing, the combination comprising:
    a. medical tubing; and
    b. a guard consisting of a soft cushion-like non-woven fiber web member having a generally rectilinear configuration with a generally uniform thickness and a first and a second opposing planar surfaces, wherein said non-woven fiber web member has a medication dispersed throughout; a continuous coating of pressure sensitive adhesive permanently attached to the first of said planar surfaces, and; a cover sheet releasably attached to said adhesive and being separable therefrom to expose said adhesive for attachment to said medical tubing so as to place said non-woven fiber web member between said medical tubing and the patient skin so that the second surface contacts and conveys said medication to the patient skin.

11. The combination of claim 10 wherein said medication is calcium undecylenate.

12. The combination of claim 10 and further comprising a medication in powder form dispersed in and carried by said non-woven fiber web member.

13. The combination of claim 10 wherein said medication is corn starch.

14. A method of avoiding chafing of patient skin by medical tubing comprising the steps of
    a. providing a guard consisting of a non-woven fiber web member of soft non-adhesive material, having a first and a second opposing planar surfaces, wherein said non-woven fiber web member has a medication dispersed throughout; and a continuous adhesive layer of uniform thickness attached to the first planar surface of said non-woven fiber web member for attachment to said medical tubing so as to place said non-woven fiber web member at a location between said medical tubing and the patient skin;
    b. attaching the guard to an outer surface of said medical tubing; and
    c. placing the guard in opposing contact between the medical appliance and patient skin.

15. A method of avoiding chafing of patient skin by medical tubing comprising the steps of
    a. providing a guard consisting of a soft cushion-like non-woven fiber web member having a generally rectilinear configuration with a generally uniform thickness and a first and a second opposing planar surfaces, wherein said non-woven fiber web member has a medication dispersed throughout; a continuous coating of pressure sensitive adhesive permanently attached to the first of said planar surfaces, and; a cover sheet releasably attached to said adhesive and being separable therefrom to expose said adhesive for attachment to said medical tubing so as to place said non-woven fiber web member between said medical tubing and the patient skin;
    b. removing releasable cover sheet to expose said continuous adhesive;
    c. attaching the guard to an outer surface of said medical tubing; and
    d. placing the guard in opposing contact between the medical tubing and patient skin.

* * * * *